(12) United States Patent
Turner

(10) Patent No.: US 6,360,794 B1
(45) Date of Patent: Mar. 26, 2002

(54) APPARATUS AND METHOD FOR DELIVERING A FLUID TO A CONTAINER

(75) Inventor: Terry D. Turner, Ammon, ID (US)

(73) Assignee: Bechtel BWXT Idaho, LLC, Idaho Falls, ID (US)

( * ) Notice: Subject to any disclaimer, the term of this patent is extended or adjusted under 35 U.S.C. 154(b) by 0 days.

(21) Appl. No.: 09/741,212

(22) Filed: Dec. 19, 2000

(51) Int. Cl.[7] .................................................. B65B 3/04
(52) U.S. Cl. ............................. 141/329; 141/1; 141/7; 141/65; 141/130; 422/63; 73/863.81; 73/863.83; 73/864.24
(58) Field of Search .......................... 141/1, 7, 65, 130, 141/329, 330; 422/63–67; 73/863.81, 863.82, 863.83, 863.84, 864.24

(56) References Cited

U.S. PATENT DOCUMENTS

| | | | | |
|---|---|---|---|---|
| 3,824,859 A | * | 7/1974 | Harris, Sr. et al. | 73/864.87 |
| 3,885,438 A | * | 5/1975 | Harris, Sr. et al. | 73/863.81 |
| 4,342,341 A | * | 8/1982 | Lee | 141/1 |
| 4,586,546 A | * | 5/1986 | Mezei et al. | 73/864.24 |
| 5,012,845 A | * | 5/1991 | Averette | 141/329 |
| 5,238,031 A | * | 8/1993 | Baeumer et al. | 141/27 |
| 5,400,666 A | * | 3/1995 | Song | 73/864.21 |
| 5,756,905 A | * | 5/1998 | Ueda | 73/864.24 |

* cited by examiner

*Primary Examiner*—J. Casimer Jacyna
(74) *Attorney, Agent, or Firm*—Klaas Law O'Meara & Malkin

(57) ABSTRACT

An apparatus for delivering a fluid into a container has a carriage movably associated with a holding mechanism along an axis. A piston is attached to the carriage and a cylinder is slidably attached to the piston along the axis. The cylinder has a hole formed therein that extends along the axis. A needle extending along the axis is attached to the piston and passes through the cylinder hole. The needle has a first operative position relative to the piston when the needle is retracted within the cylinder and a second operative position relative to the piston when the needle extends from the cylinder.

24 Claims, 7 Drawing Sheets

APPARATUS AND METHOD FOR DELIVERING A FLUID TO A CONTAINER

CONTRACTUAL ORIGIN OF THE INVENTION

This invention was made with United States Government support under Contract No. DE-AC07-94ID13223, now Contract No. DE-AC07-99ID13727 awarded by the United States Department of Energy. The United States Government has certain rights in the invention.

TECHNICAL FIELD

The present invention relates to an apparatus and method for filling containers and, more particularly, to an automated apparatus and method for filling septum-sealed containers.

BACKGROUND OF THE INVENTION

Septum-sealed containers are often used to store sterile or hazardous fluids. Sterile liquids, such as medicines, require special handling and storage precautions so that they do not contact the environment and become contaminated. Other liquids, such as environmental samples, also require special handling precautions so that the samples do not become contaminated. Likewise, hazardous liquids require special handling and storage precautions so that they do not escape into and contaminate the environment. In order to prevent these liquids from coming into contact with the environment, they are typically stored in a septum-sealed container, such as a septum-sealed vial. The septum of a septum-sealed vial is typically made from a pliable polymer, such as a rubber material, that is readily pierced by a needle and that seals itself upon removal of the needle. The needle is used to pierce the septum in order to add fluids to the vial. Likewise, the needle may be used to pierce the septum in order to remove fluids from the vial. When the needle pierces the septum, it forms a hole that is just wide enough to allow the needle to pass through the septum. The pliability of the septum creates a seal between the needle and the septum when the needle is in the septum. This seal prevents the fluid within the vial from contacting the environment when the needle is in the septum. An objective in piercing the septum is to avoid ripping or otherwise damaging the septum, which would prevent the septum from sealing with the needle. Likewise, another objective in piercing the septum is to assure that the hole created by the needle seals itself upon removal of the needle, which prevents the fluid within the container from being exposed to the environment.

In some applications, automated filling devices are used to fill the vials. For example, a drug company may use an automated filling device to fill septum-sealed vials with sterile drugs. Other industries may use automated filling devices that are remote from human intervention to keep operators from exposure to the fluids. For example, in a situation where hazardous fluids are required to be delivered to a container, it is generally safer to handle these containers without human exposure to the liquids.

These automated filling devices, however, have several disadvantages. One disadvantage with automated filling devices is that they have a tendency to move the container relative to the needle as the needle pierces the septum. This movement of the container relative to the needle can damage the needle, the septum, or both. If the septum becomes damaged, it will not properly seal the container and the fluid within the container will be exposed to the environment. Another disadvantage with automated filling devices is that they do not provide for easy cleaning of the needle. An unclean or contaminated needle may contaminate the fluid within the container.

Therefore, a need exists for an automated container filling device that does not damage septa used to seal the containers and that may be easily cleaned.

SUMMARY OF THE INVENTION

The present invention is directed toward an apparatus and method for delivering fluids into a container. The apparatus has a holder mechanism and a carriage, wherein the carriage is movable along an axis relative to the holder mechanism. The holder mechanism serves to hold the container in a fixed position during the filling process. The carriage has a piston attached to it and a cylinder having a hole formed therein is slidably attached to the piston along the axis. A needle extending along the axis is attached to the piston and passes through the hole in the cylinder. The association between the piston and the cylinder forms a chamber within the cylinder. The needle has a first operative position relative to the cylinder when the chamber has a first volume and the needle has a second operative position relative to the cylinder when the chamber has a second volume. In the first operative position, the needle may, as a non-limiting example, be recessed within the cylinder. In the second operative position, the needle may, as a non-limiting example, extend from the cylinder.

Using the apparatus to deliver a fluid to a container involves moving the carriage along the axis away from the holder mechanism. The chamber within the cylinder is filled with a fluid, which causes the cylinder to move toward the holding mechanism and sheaths the needle within the cylinder. A container may then be placed on the holding mechanism without the container inadvertently contacting the needle. The carriage is then moved along the axis toward the container to a point where the cylinder contacts the container. The movement of the carriage along the axis toward the holder mechanism continues as the fluid within the chamber is vented, which reduces the volume of the chamber and allows the needle to extend from the cylinder. The force exerted on the container by the cylinder is proportional to the rate at which the fluid is vented from the cylinder and the rate at which the carriage moves toward the container. When the needle has entered the container, a fluid is passed through the needle and into the container. In the situation where the container has a septum seal, the needle pierces the septum as the fluid is vented from the chamber.

Removing the needle from the container commences with filling the chamber with a fluid, which increases the volume of the chamber. Increasing the volume of the chamber maintains a force on the container exerted by the cylinder, and causes the piston and carriage to move away from the container. As the piston moves away from the container, the needle attached to the piston is removed from the container. When the needle has been removed from the container, the carriage is moved along the axis away from the container. The above-described force applied to the container assures that a septum pierced by the needle is not damaged by movement of the container relative to the needle as the needle is removed from the septum.

An embodiment of the above-described apparatus also provides for a mechanism that cleans the needle. The holder mechanism has a first hole formed therein that is positioned to receive the needle. A second hole in the holder mechanism intersects the first hole. During the cleaning process, the carriage and cylinder are moved so that the needle is positioned in the first hole. Cleaning solutions are injected through the needle or the second hole to clean the needle.

DETAILED DESCRIPTION OF THE INVENTION

Figure 1:
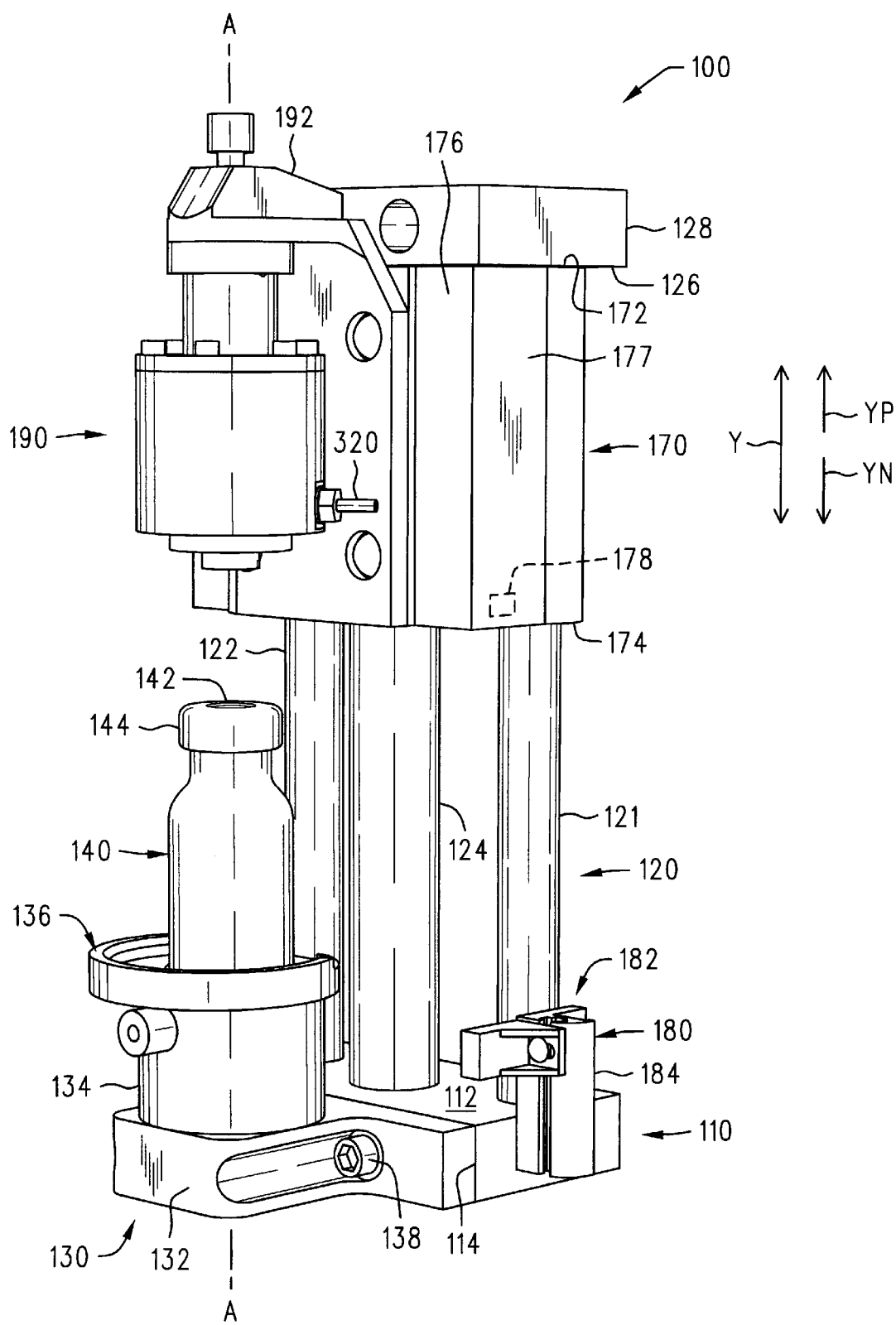
FIG. 1 is a side perspective view of a filling apparatus with a container located therein.

A side perspective view of a non-limiting embodiment of a filling apparatus or device 100 is illustrated in FIG. 1. The filling device 100 has a base portion 110 wherein the base portion 110 has a top surface 112 and a side surface 114. The base portion 110 is fabricated from a durable material, such as steel or aluminum. A plurality of rails 120 are attached to and extend perpendicular from the top surface 112 of the base portion 110. For illustration purposes, reference is made to an axis AA wherein the rails 120 are parallel to the axis AA. The non-limiting embodiment of the filling device 100 of FIG. 1 has two rails 120, a first rail 121 and a second rail 122 attached to the base portion 110. In addition to the rails 120, a pneumatic cylinder 124 is attached to and extends perpendicular from the top surface 112 of the base portion 110. The pneumatic cylinder 124 is parallel to the rails 120. The rails 120 and the pneumatic cylinder 124 are attached to a lower surface 126 of a top portion 128 of the filling device 100.

A holding mechanism 130 is removably attached to the side surface 114 of the base portion 110. The holding mechanism 130 has a support piece 132 with an extension member 134 attached thereto. A tray 136 is attached to the extension member 134 opposite the support piece 132. A plurality of screws, one of which is shown in FIG. 1 and is referenced as screw 138, removably attach the support piece 132 to the base portion 110. The screws provide for simple exchange and cleaning of the holding mechanism 130.

The holding mechanism 130 serves to hold containers in a fixed position while they are being filled by the filling device 100. The filling device 100 illustrated in FIG. 1 has a container 140 positioned on the extension member 134 within the tray 136 of the holding mechanism 130. The container 140, as described herein, in a non-limiting embodiment, is a vial that is sealed by a septum 142, e.g., a conventional rubber septum seal. The septum 142 is held in place over an opening in the container 140 by means of a conventional ring 144. It should be noted that containers other than septum-sealed containers, e.g., open beakers, may be used in conjunction with the filling device 100.

Figure 2:
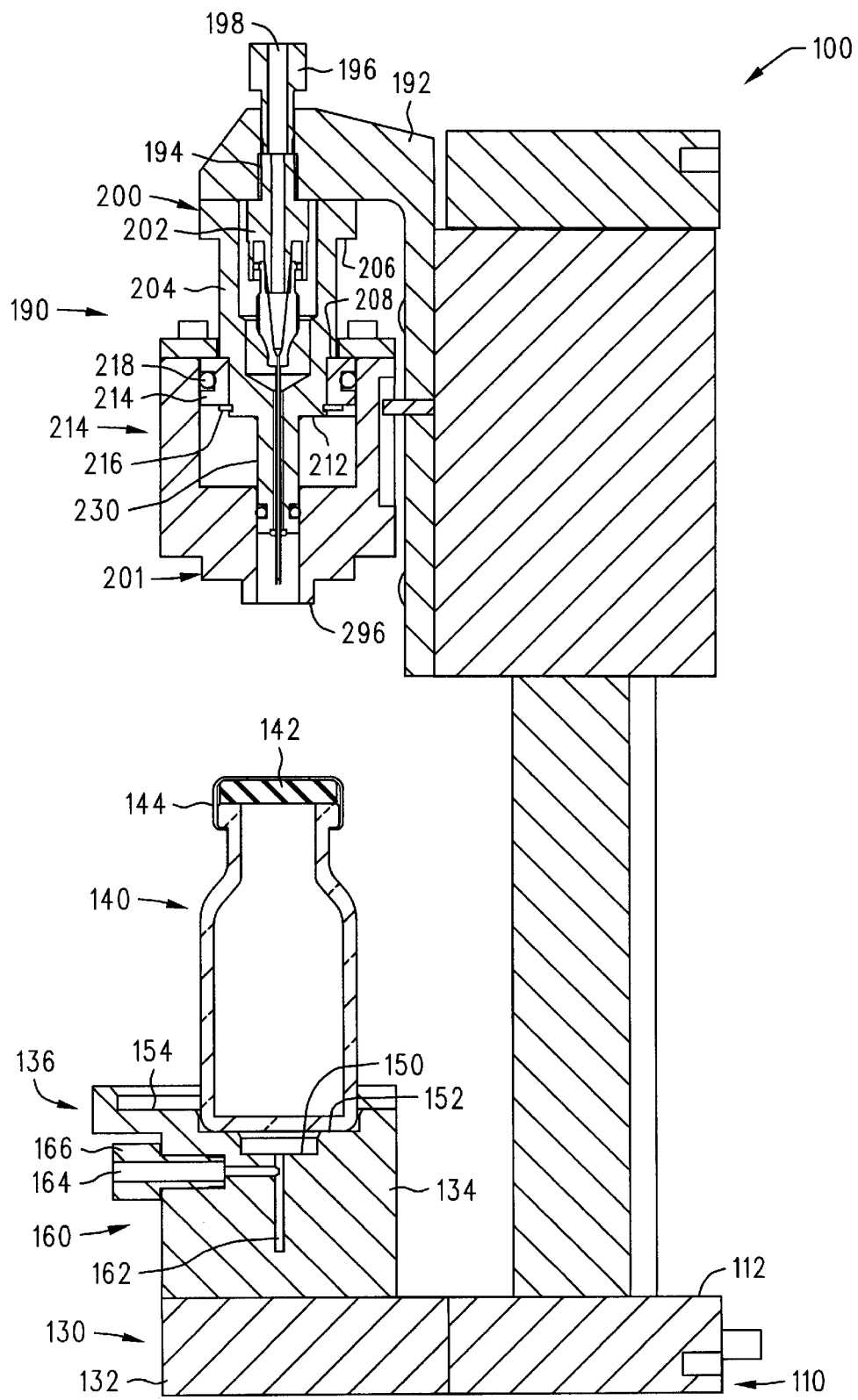
FIG. 2 is a side sectional view of the filling apparatus of FIG. 1.

A more detailed illustration of the holding mechanism 130 is shown in FIG. 2, which is a side sectional view of the filling device 100. As shown in FIG. 2, the tray 136 has a plurality of tiers that serve to hold various sized and shaped containers. The non-limiting embodiment of the tray 136 illustrated herein has three tiers, a first tier 150, a second tier 152, and a third tier 154. In a non-limiting example of the tray 136, the first tier 150 is appropriately sized and shaped to accommodate a conventional one milliliter container, e.g., a vial or beaker. The second tier 152 is appropriately sized and shaped to accommodate a conventional ten milliliter vial and the third tier 154 is appropriately sized and shaped to accommodate a conventional fifty milliliter beaker.

A drain system 160 is formed into the extension member 134 of the holding mechanism 130. The drain system 160 has a vertical channel 162 and a horizontal channel 164. As shown in FIG. 2, the vertical channel 162 extends downward from the first tier 150 and terminates inside the extension member 134. The horizontal channel 164 extends between the exterior of the extension member 134 and the vertical channel 162. As will be described in greater detail below, the vertical channel 162 is appropriately sized to accommodate a needle that is used to deliver a fluid into the container 140.

The horizontal channel 164 passes through a coupling 166. The coupling 166 allows an external hose or tube to be attached to the horizontal channel 164. This hole or tube may serve to drain liquids or gasses from the vertical channel 162 and the horizontal channel 164. For example, air may be blown into the channel 164 or a vacuum may be pulled on the horizontal channel 164 for cleaning purposes as described below. A valve, not shown in FIG. 2, may be attached to the horizontal channel 164 and may serve to regulate the flow of liquids and gasses through the horizontal channel 164.

Referring again to FIG. 1, a carriage 170 is slidably attached to the rails 120 and the cylinder 124. The carriage 170 has an upper surface 172, a lower surface 174, a front portion 176 and a side portion 177. The carriage 170 slides on the rails 120 along the axis AA in the y-direction Y. The cylinder 124 serves to move the carriage in the y-direction Y along the rails 120. The y-direction Y is described in greater detail herein with reference to a positive y-direction YP and a negative y-direction YN. The movement of the carriage 170 in the positive y-direction YP is limited by the top portion 128. More specifically, as the carriage 170 moves in the positive y-direction YP, the upper surface 172 of the carriage 170 will eventually come into close proximity with, or contact, the lower surface 126 of the top portion 128. Likewise, as the carriage 170 moves in the negative y-direction YN, its lower surface 174 will eventually come into close proximity with, or contact, the top surface 112 of the base portion 110. In one embodiment of the carriage 170, a magnet 178 is embedded into the side portion 177 of the carriage 170. As described below, the magnet 178 is used to determine the position of the carriage 170 relative to the base portion 110.

A position sensor 180 that, in conjunction with the magnet 178, serves to sense the location of the carriage 170, is attached to the base portion 110. In the non-limiting embodiment disclosed herein, the position sensor 180 has a hall effect switch 182 attached to a vertical member 184. The member 184 serves to position the switch 182 at a preselected height above the top surface 112 of the base portion 110. The switch 182 is toggled as the magnet 178 passes by it in a conventional manner. Accordingly, the toggling of the switch 182 serves to sense the presence and, thus, the approximate vertical position of the carriage 170 relative to the switch 182 and the top surface 112 of the base portion 110. The output of the position sensor 180 may, as an example, be transmitted to a processor that controls the movement of the carriage 170. It should be noted that other types of position sensors may be used within the filling device 100 and that other position sensors may be used throughout the filling device 100 to identify the locations of movable components described herein.

Figure 3:
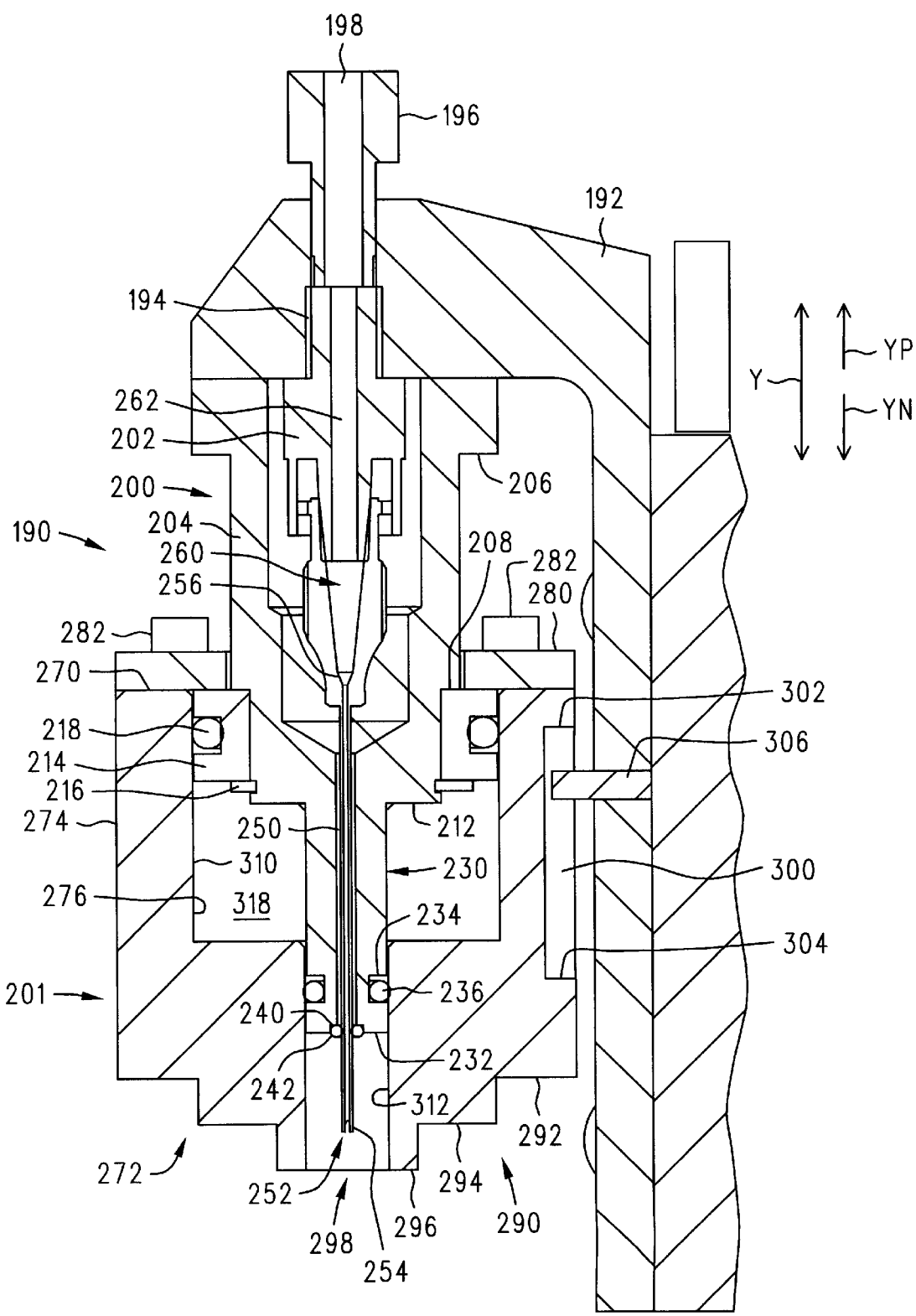
FIG. 3 is a detailed, sectional view of the cylinder assembly of FIG. 2.

A cylinder housing assembly 190, sometimes herein referred to simply as the cylinder assembly 190, is attached to the carriage 170 so as to be adjacent the front portion 176 of the carriage 170. More specifically, a fixture 192 extends from the front portion 176 of the carriage 170 and attaches the cylinder assembly 190 to the carriage 170. The cylinder assembly 190 is illustrated in greater detail in FIG. 3, which is an enlarged view of the cylinder assembly 190. As shown in FIG. 3, the fixture 192 has a threaded hole 194 formed therein. A coupling 196 having a hole 198 passing S therethrough is threaded into the threaded hole 194. As described in greater detail below, the coupling 196 attaches to a delivery system that delivers a fluid to the container 140, FIG. 1. The delivery system may also pull a vacuum on the container 140, FIG. 1. The coupling and components associated therewith may, as a non-limiting example, be adapted to accommodate luer fittings and components.

The cylinder assembly 190 has a piston 200 that is rigidly attached to the fixture 192. A cylinder 201 is movably attached to the piston 200 along the axis AA, FIG. 1, in the y-direction Y. The piston 200 has an inner portion 202 and an outer portion 204, wherein part of the inner portion 202 is threaded into the threaded hole 194. The outer portion 204 has a plurality of substantially cylindrical portions having a first step 206, a second step 208, and a lower surface 212, which are described in greater detail below.

A piston ring 214 surrounds the outer portion 204 of the piston 200 in the vicinity of the lower surface 212 and abuts the second step 208. The piston ring 214 is retained in a fixed position relative to the piston 200 by the use of a clip 216. The piston ring 214 has a cut out with a gasket 218 located therein. The gasket 218 may, as an example, be a conventional o-ring type gasket. As described below, the piston ring 214 serves to limit the movement of the cylinder 201 relative to the piston 200. The gasket 218 serves to form a seal between the cylinder 201 and the piston 200 to keep a fluid within the cylinder 201 from seeping out of the cylinder assembly 190.

A cylindrical shaft 230 extends from the lower surface 212 of the piston 200. The shaft 230 has a substantially planar end 232 through which a needle 252 extends as is described in detail below. The shaft 230 has a groove 234 located in the proximity of the end 232 that extends over the circumference of the shaft 230. A gasket 236, i.e., an o-ring type gasket, is located in the groove 234. The gasket 236 serves to maintain a seal between the piston 200 and the cylinder 201. A cutout 240 is located on the end 232 of the shaft 230 and has a gasket 242, i.e., an o-ring type gasket, located therein. The gasket 242 serves to form a seal between the needle 252 and the shaft 230 One purpose of the gasket 242 is to prevent fluids from leaking into or out of the interior portion of the piston 200.

A channel 250 is formed within the shaft 230 and extends the length of the shaft 230. The channel 250 is appropriately sized to hold the needle 252 in a fixed position relative to the shaft 230. The needle 252 has a first end 254 and a second end 256. The first end 254 of the needle 252 is adapted to penetrate the septum 142, FIG. 1, of the container 140. For example, the first end 254 of the needle 252 may have a point formed therein that is similar to a conventional hypodermic needle. The needle 252 may, as a further non-limiting example, be a twenty-gauge luer lock needle or luer lock syringe.

The needle 252 is retained in a fixed position within the piston 200 by a needle holder 260. More specifically, the second end 256 of the needle 252 is retained within the inner portion 202 of the piston 200 by the needle holder 260. The needle holder 260 may, as a non-limiting example, be adapted to receive a luer lock syringe or needle. The needle holder 260 is hollow and is attached to a tube 262. The tube 262 extends between the needle holder 260 and the hole 198 in the coupling 196. To follow the examples of luer components, the tube 262 and the coupling 196 may be luer components. Accordingly, a path for fluids exists between the coupling 196 and the first end 254 of the needle 252. As described below, this path is used to deliver fluids to containers and to clean the needle 252.

Having described the piston 200, the cylinder 201 will now be described. The cylinder 201 has an upper portion 270, a lower portion 272, an outer surface 274, and an inner surface 276. The upper portion 270 has a retaining ring 280 (sometimes referred to as a protrusion) attached thereto by the use of a plurality of screws 282. The retaining ring 280 has a diameter that is smaller than the diameter of the inner surface 276 of the cylinder 201. The diameter of the retaining ring 280 is slightly greater than the diameter of the piston 200, which allows the piston 200 to move through the retaining ring 280. As will be described in greater detail below, the retaining ring 280 serves to limit the movement of the cylinder 201 relative to the piston 200 in the y-direction Y. The lower portion 272 of the cylinder 201 has a plurality of tiers 290 formed therein. The tiers 290 consist of a first tier 292, a second tier 294, and a third tier 296. The third tier 296 has a hole 298 formed therein, which is appropriately sized to accommodate the shaft 230 of the piston 200. As will be described below, the tiers 290 serve to retain the container 140, FIG. 1, in a fixed position as the container 140 is being filled.

The outer surface 274 of the cylinder 201 has a groove 300 formed therein. The groove 300 extends a preselected distance in the y-direction Y and has an upper surface 302 and a lower surface 304. The groove 300 is appropriately sized to receive a pin 306 that extends from the fixture 192. As will be described in greater detail below, the groove 300, in conjunction with the pin 306, serves to limit the movement of the cylinder 201 relative to the fixture 192 in the y-direction Y. The pin 306 also serves to keep the cylinder 201 from rotating relative to the piston 200.

The inner surface 276 of the cylinder 201 has a first surface 310 and a second surface 312, both of which are relatively smooth to accommodate movement of the piston 200. The first surface 310 provides for movable contact between the piston ring 214 and the cylinder 201. The second surface 312 provides for movable contact between the shaft 230 and the cylinder 201. A chamber 318 is formed within the cylinder 201 between the first surface 310 and the piston 200. The chamber 318 is sealed by the gasket 218 and the gasket 236. An inlet, not shown in FIG. 3, provides a venting means to allow predetermined volumes of fluid in and out of the chamber 318. The inlet is connected to a vent 320, FIG. 1, located on the cylinder assembly 190. The vent 320 serves to connect 17 the chamber 318, FIG. 3, to a fluid regulator, not shown. The fluid regulator controls the amount and pressure of fluid within the chamber 318. This control is achieved by regulating the flow of fluid into and out of the chamber 318. It should be noted that the term fluid applies to both liquids and gases.

Referring again to FIGS. 1 and 2, having described the components of the filling device 100, its operation will now be described.

FIGS. 1 and 2 show the filling device 100 in a container access mode, which is the default position of the filling device 100. The container access mode is sometimes referred to as the first operative position of the filling device 100. The container access mode allows containers to be placed into the holding mechanism 130. In this mode, the carriage 170 is moved in the positive y-direction YP to a point where the upper surface 172 of the carriage 170 is adjacent the lower surface 126 of the top portion 128. More specifically, the cylinder 124 is used to move the carriage 170 along the rails 120 to a point where the upper surface 172 of the carriage 170 is adjacent the lower surface 126 of the stop 128.

Referring again to FIG. 3, in the container access mode, the cylinder 201 is moved in the negative y-direction YN relative to the piston 200 as is shown in FIG. 3. The position of the piston 200 relative to the cylinder 201 is achieved by increasing the size of the chamber 318. This expansion may be achieved by creating a positive pressure within the chamber 318, which forces the piston 200 and the cylinder 201 apart. For example, referring briefly to FIG. 1, a fluid, such as air, may be forced into the chamber 318 via the vent 320. Alternatively, gravity may force the cylinder 201 to fall in the negative y-direction YN relative to the piston 200, which expands the chamber 318. When the chamber 318 is expanded, the needle 252 is sheathed within the hole 298 in the cylinder 201. This sheathed position of the needle 252 prevents an operator from inadvertently contacting the needle 252 as the container 140, FIG. 1, is placed onto or removed from the holding mechanism 130. This sheathed position of the needle 252 also prevents the container 140 from improperly contacting the needle 252, which could damage the needle 252 or the container 140. In the case of a septum-sealed container, contact with the needle 252 can damage the septum seal. The movement of the cylinder 201 relative to the piston 200 in the negative y-direction YN is limited by the piston ring 214 contacting the retaining ring 280 as shown in FIG. 3.

Referring again to FIGS. 1 and 2, the container 140 is placed onto the holding mechanism 130. A user or a robotic instrument may place the container 140 onto the tray 136. The container 140 illustrated herein is, as a non-limiting example, a ten milliliter vial of the type used in the environmental industry for sample collection. The second tier 152 of the holding mechanism 130 is appropriately sized and shaped to hold the container 140. It should be noted that other containers having sizes and shapes corresponding to the first tier 150 and the third tier 154 may also be used by the filling device 100 illustrated herein. It should also be noted that the tiers may be formed to hold virtually any sized or shaped container. In the event that the proper tier is not formed into the holding mechanism 130, the holding mechanism 130 may be readily replaced with a holding mechanism that has a proper tier formed therein.

Figure 4:
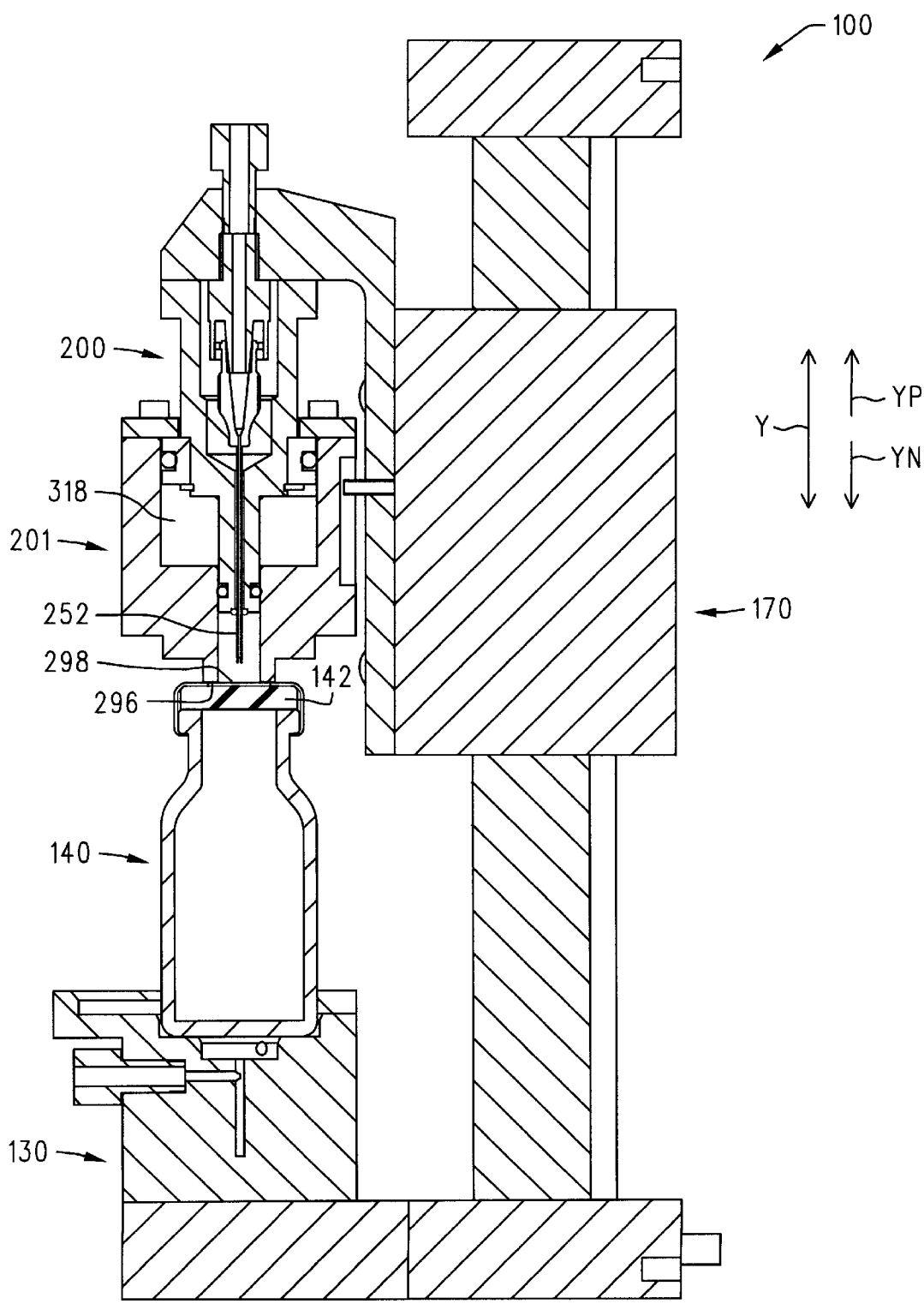
FIG. 4 is a side sectional view of the filling apparatus of FIG. 2 in a second operative mode securing a container to be filled.

Referring to FIG. 4, after the container 140 is placed within the holding mechanism 130, the cylinder 124 moves the carriage 170 in the negative y-direction YN to a point where the third tier 296 of the cylinder 201 contacts the septum 142 of the container 140. This configuration of the filling device 100 is sometimes referred to herein as the second operative mode of the filling device 100. The position or at least the approximate position of the carriage 170 may be sensed by position sensors, not shown in FIG. 4. The position of the carriage 170 may also be sensed by an increase in the force required to move the carriage 170 in the negative y-direction YN, which is indicative of the cylinder 201 contacting the container 140. The force exerted by the cylinder 201 on the container 140 is enough to prevent the container 140 from moving relative to the filling device 140 during the filling process. The force, however, is not great enough to damage the septum 142 or other portions of the container 140. It should be noted that the flat surface of the third tier 296 distributes the force onto the container 140 and lessens the probability of the cylinder 201 damaging the septum 142.

As the above-described force is applied to the container 140, the cylinder 201 remains extended in the negative y-direction YN relative to the piston 200 by maintaining the chamber 318 at a relatively large size. For example, positive pressure may be maintained within the chamber 318. This positive pressure serves to retain the container 140 in a fixed position as well as to retain the needle 252 within the hole 298 of the cylinder 201 as the cylinder 201 contacts the container 140.

Figure 5:
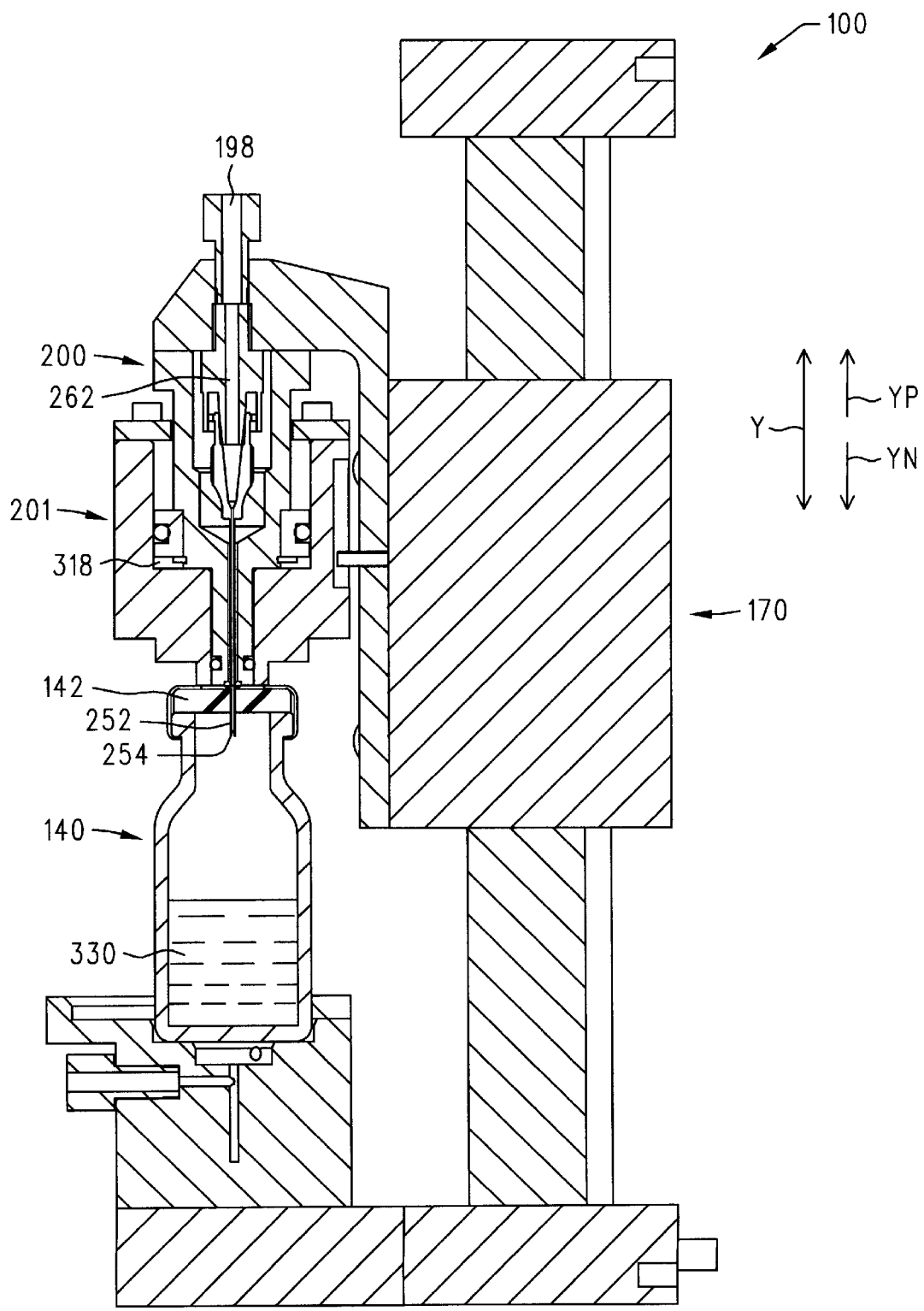
FIG. 5 is a side sectional view of the filling apparatus of FIG. 2 in a third operative mode filling a container.

At this point in the filling cycle, the container 140 is properly secured within the holding mechanism 130 and is ready to be filled by having the needle 252 pierce the septum 142. FIG. 5 illustrates the filling device 100 in a third operative mode wherein the needle 252 has pierced the septum 142 of the container 140. The container 140 may then be filled by passing a fluid through the needle 252 as described below. In order to obtain the configuration shown in FIG. 5, the carriage 170 is moved further in the negative y-direction YN. As the carriage 170 moves, the vent 320, FIG. 1, is opened to allow release of the fluid within the chamber 318, which allows the piston 200 to move in the negative y-direction YN relative to the cylinder 201. As the piston 200 moves relative to the cylinder 201, the first end 254 of the needle 252 contacts and pierces the septum 142 of the container 140. Because the cylinder 201 maintains the container 140 in a fixed position, the needle 252 pierces the septum 142 without moving relative to the septum 142. Accordingly, neither the septum 142 nor the needle 252 become damaged during the piercing.

After the needle 252 has pierced the septum 142, the container 140 may be filled. It should be noted that some containers are required to be evacuated prior to being filled. Prior to filling these containers, a vacuum is drawn from the hole 198, which as described above is connected to the first end 254 of the needle 252. Accordingly, a vacuum is created within the container 140. A liquid 330 is then passed through the hole 198, the tube 262, the needle 252, and into the container 140. It should be noted that a gas may also be passed into the container 140 by a similar method. As described above, a fluid control system, not shown, may be connected to the hole 198 to regulate the vacuum and delivery of the fluid into the container 140. It should also be noted that the filling device 100 may be used to remove a fluid from the container 140 by drawing the fluid through the needle 252 and out the hole 198.

After the container 140 has been filled, the needle 252 needs to be removed from the septum 142 and the carriage 170 needs to be moved in the positive y-direction YP away from the container 140. Removal of the needle 252 from the septum 142 must be accomplished so as not to damage the septum 142 or the needle 252. Removal of the needle 252 is accomplished by maintaining the container 140 in a fixed position relative to the needle 252 as the needle 252 is removed from the septum 142. A preselected force in the negative y-direction YN is applied by the cylinder 124 to the carriage 170. This preselected force acts between the cylinder 201 and the container 140 to retain the container 140 in a fixed position relative to the holding mechanism 130. A fluid is then forced into the chamber 318 via the vent 320, FIG. 1, creating pressure therein. The pressure causes a force to be exerted between the piston 200 and the cylinder 210 that forces them apart in the y-direction Y. This force acts between the cylinder 201 and the container 140 and serves to maintain the container 140 in a fixed position as the needle 252 is removed from the septum 142. Eventually, the force exerted by the pressure in the chamber 318 overcomes the force in the negative y-direction YN exerted by the carriage 170 on the cylinder 201. As this occurs, the piston 200 and the carriage 170 move in the positive y-direction YP and the cylinder 201 remains abutted against the container 140. Accordingly, the needle 252 moves in the positive y-direction YP out of the septum 142 and into the cylinder 201.

Referring again to FIG. 4, when the filling device 100 determines that the piston 200 is at a preselected position relative to the cylinder 201, the carriage 170 is moved in the positive y-direction YP. For example, a position sensor, not shown in FIG. 4, may detect the position of the cylinder 201 relative to the piston 200. As described above, the position sensor may determine the approximate position of the cylinder 201 relative to the piston 200. This preselected position is a point where the cylinder 201 has moved far enough relative to the piston 200 so that the needle 252 is sheathed within the hole 298. After the needle 252 has been removed from the septum 142 and has been sheathed within the cylinder 201, the carriage 170 is moved in the positive y-direction YP away from the container 140. The filling device 100 is then in the first operative mode as described above and as shown in FIGS. 1 and 2. At this point, the filled container 140 may be removed from the holding mechanism 130. A new container may be placed onto the holding mechanism 130 and filled as described above. During removal and addition of containers to the holding mechanism 130, the needle 252 remains sheathed, which prevents their septa from becoming damaged by the needle 252.

Referring briefly to FIG. 5, it should be noted that during the filling process, only the needle 252, the tube 262, and the coupling 196 contact the liquid 330 that is delivered into the container 140. In the event the liquid 330 is hazardous, it will only contaminate a minimal number of components within the filling device 100. In addition, in the event that the container 140 is filled with a hazardous liquid to which another liquid is added by implementation of the above procedure, only the needle 252 has a chance of becoming contaminated. Likewise, if the liquid 330 is sterile, it has a relatively low probability of becoming contaminated by the filling device 100 because it only contacts a limited 55 number of components during the filling process.

Figure 6:
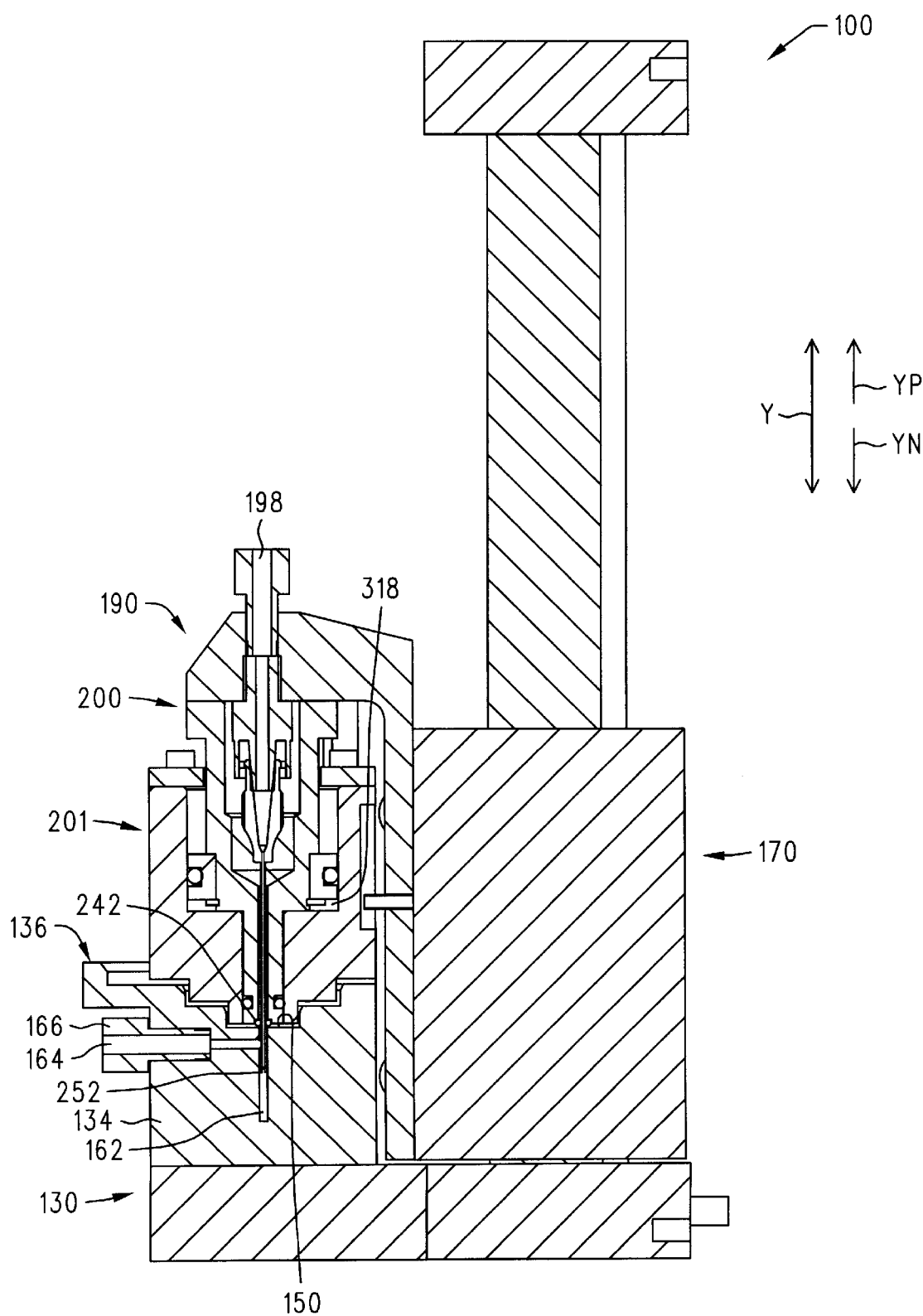
FIG. 6 is a side sectional view of the filling apparatus of FIG. 2 in a fourth operative mode cleaning the needle.

Referring to FIG. 6, the filling device 100 is able to automatically clean the needle 252 subsequent to the removal of the container 140, FIG. 5, from the holding mechanism 130. As shown in FIG. 6, the carriage 170 is moved in the negative y-direction YN to the proximity of the holding mechanism 130. The proximity of the holding mechanism 130 may, as a non-limiting example, be sensed by the position sensor 180, FIG. 1, in conjunction with the magnet 178, FIG. 1. The size of the chamber 318 is reduced as described above so that the needle 252 extends beyond the cylinder 201 and into the vertical channel 162. This configuration of the filling device 100 is sometimes referred to as the fourth operative mode of the filling device 100.

In this fourth operative mode, the cylinder 201 is located adjacent or contacts the tray 136. The gasket 242 contacts the first tier 150 of the tray 136 and, in combination with the needle 252, seals the vertical channel 162 from the cylinder assembly 190. A cleaning solvent is delivered to the vertical channel 162 and the horizontal channel 164 of the drain system 160 via the hole 198. More specifically, the cleaning solvent may pass through the needle 252 as described above with reference to the fluid 330, FIG. 5 added to the container 140. The cleaning solvent serves to remove contaminants from the needle 252. The cleaning solvent is removed from the drain system 160 by pulling a vacuum on the horizontal channel 164. Accordingly, the needle 252 is cleaned automatically without the need to disassemble the filling device 100. It should be noted that the needle 252 may be further cleaned by forcing air into the hole 198 so that it exhausts through the needle 252 and into the drain system 160. This process of forcing air into the hole 198 may also be used to remove the cleaning solvent from the drain system 160. The needle 252 and the filling systems attached thereto may also be cleaned by forcing the cleaning solvent into the hole 198 so that it exhausts out the first end 254 of the needle 252.

Figure 7:
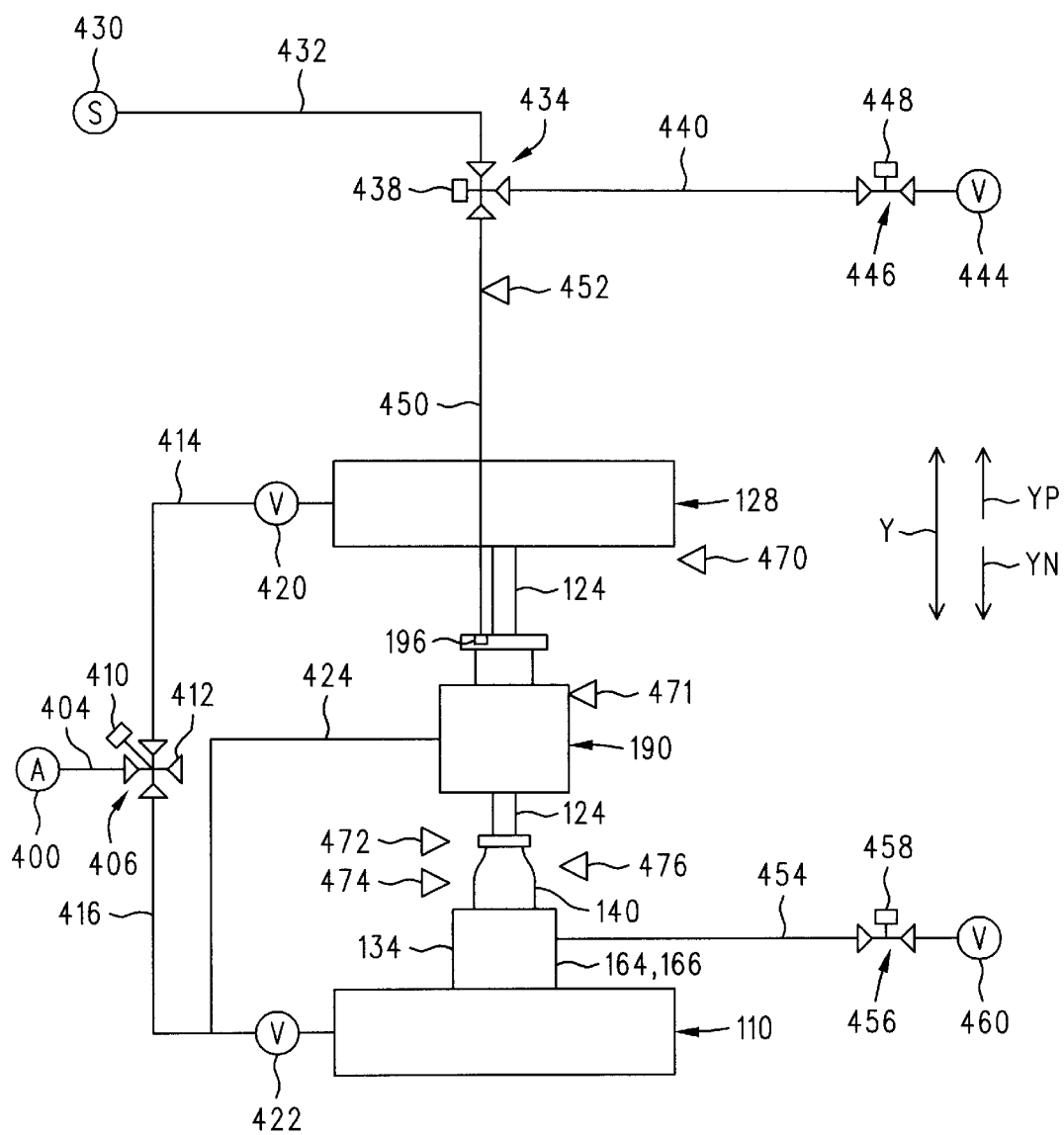
FIG. 7 is a schematic illustration of the pneumatic systems of the filling apparatus of FIG. 1.

Having described the filling device 100, fluid lines external to the filling device 100 will now be described. FIG. 7 illustrates a non-limiting example of the fluid lines that may be associated with the filling device 100. An air supply 400 supplies air via an air line 404 to a valve 406. The operation of the valve 406 is controlled by a solenoid 410. A vent 412, a first air line 414, and a second air line 416 are connected to the valve 406. The valve 406 operates by actuation of the solenoid so that the air line 404 is connected to either the first air line 414 or the second air line 416. The air line 414 or 416 that is not connected to the air line 404 is connected to the vent 412.

The first air line 414 passes through a valve 420 and into the top portion 128 of the filling device 100. The second air line 416 passes through a valve 422 and into the base portion 110. Both the first air line 414 and the second air line 416 are connected to the pneumatic cylinder 124. By forcing air into the pneumatic cylinder 124 from the top portion 128, the pneumatic cylinder causes the carriage 170 to move in the negative y-direction YN. By forcing air into the pneumatic cylinder 124 from the base portion 110, the pneumatic cylinder 124 causes the carriage 170 to move in the positive y-direction YP. An air line 424 is connected to the second air line 416. The air line 424 serves to fill or vent the chamber 318, FIG. 3, of the cylinder assembly 190.

Having described the components that control the movement of the cylinder assembly 190, their operation will now be described. Referring to both FIGS. 2 and 7, the movement of the carriage 170 and, thus, the cylinder assembly 190 will be described as commencing from the first operative position as shown in FIG. 2 and moving in the negative y-direction YN. The solenoid 410 activates to connect the air line 404 to the first air line 414. Accordingly, the air supply 400 is connected to the upper portion of the pneumatic cylinder 124 through the valve 420. The second air line 416 and, thus, the lower portion of the pneumatic cylinder 124 is connected to the vent through the valve 422. In this mode, the valve 420 serves as a check valve to assure that air flows into and not out of the top portion of the pneumatic cylinder 124. The valve 422 serves as a needle valve to regulate the flow of air out of the lower portion of the pneumatic cylinder 124. Accordingly, positive air pressure is created in the top portion of the pneumatic cylinder 124, which causes the cylinder assembly 170 to move in the negative y-direction YN. The movement is regulated by the amount of air flowing through the valve 422.

The air line 424 and, thus, the chamber 318, FIG. 2, are connected to the vent 412. As the cylinder assembly 170 moves in the negative y-direction YN, it eventually contacts the container 140 as shown in FIG. 4. Because the chamber 318 is open to the vent 412, the piston 200 is free to move into the cylinder 201 as illustrated in FIG. 5, which reduces the volume of the chamber 318. The vent 412 may be regulated so that air does not freely exhaust from the cylinder 201 in order to maintain a force on the container 140 to prevent it from moving. As described above, as the piston 200 moves into the cylinder 201, the needle 252 pierces the septum 142 on the top of the container 140. The process of filling the container 140 is described below with regard to the fluid filling lines.

After the container is filled, the needle 252 must be extracted from the container 140 without moving the container 140 and the cylinder assembly 170 must be moved to the position as illustrated in FIG. 1. The above-described actions are accomplished by activation of the solenoid 410, which causes the air supply 400 to be connected to the second air line 416 and the vent 412 to be connected to the first air line 414. It follows that the air supply 400 is also connected to the chamber 318, FIG. 5. In this situation, the valve 420 serves as a needle valve to meter the air flow from the upper portion of the pneumatic cylinder 124. The valve 422 serves as a check valve that allows air to flow into the lower portion of the pneumatic cylinder 124.

Positive air pressure is created within the chamber 318, which forces the piston 200 and the cylinder 201 apart. This forcing also forces the cylinder 201 against the container 140, which serves to maintain the container 140 in a fixed position as the needle 252 is removed from the container 140. When the chamber is fully expanded, air pressure builds in the lower portion 140 of the pneumatic cylinder 124, which causes the cylinder assembly 190 to move in the positive y-direction YP. This movement ceases when the cylinder assembly 190 is in the first operative position illustrated by FIG. 1.

Having described the lines associated with the operation of the pneumatic cylinder 124 and the cylinder assembly 190, the lines associated with filling the container 140 will now be described. The components described below are sometimes broadly referred to as fluid control devices. The following description includes a system to evacuate the container 140 prior to adding a fluid. A source 430 supplies the fluid that is to be placed into the container 140. The source 430 is connected by a fluid line 432 to a valve 434. The valve 434 is controlled by a solenoid 438. One side of the valve 434 is connected to a fluid line 440, which in turn is connected to a vacuum 444 by way of a valve 446. The valve 446 is actuated by a controller 448. Another fluid line 450 connects the valve 434 to the coupling 196 located on the cylinder assembly 190. As shown in FIG. 3, and described above, the coupling 196 connects to the needle 252. A fluid sensor 452 monitors the fluid line 450 to detect the presence of fluid in the fluid line 450.

The process of filling the container 140 commences after the needle 252, FIG. 5, has pierced the septum 142. At this point, the filling process, in one embodiment, starts with evacuating the container 140. This evacuation is accomplished by activating the valve 434 so that the fluid line 450 is connected to the fluid line 440 and, thus, the vacuum 444. The controller 448 is also activated to open the valve 446, which causes the vacuum 444 to evacuate the container 140. When the container 140 has been sufficiently evacuated, the controller 448 closes the valve 446, which separates the vacuum 444 from the container 140.

The fluid is introduced into the container 140 by actuating the solenoid 438, which connects the fluid line 450 to the fluid line 432. Accordingly, the source 430 is connected to the container 140. The source 430 delivers the fluid into the container 140 via the fluid line 432 and the fluid line 450. It should be noted that in many situations, a vacuum is not present within the container 140. Accordingly, the fluid is typically delivered to the container 140 by the use of positive pressure. As the fluid is being delivered to the container 140, the fluid sensor 452 monitors the fluid line 450. In the event the fluid sensor 452 detects that no fluid is in the fluid line 450, the delivery of fluid into the container 140 is terminated. It should be noted that the closed controller 448 prevents any fluid from being pulled into the vacuum 444 as fluid is delivered to the container 140.

Having described the filling system, the cleaning system will now be described. A fluid line 454 is connected to the horizontal channel 164 in the extension member 134 by way of the coupling 166. The fluid line 454 is connected to one side of a valve 456 that is controlled by a solenoid 458. The other side of the valve 456 is connected to a second vacuum 460. Referring additionally to FIG. 6, during the cleaning process, the cylinder assembly 190 is positioned so that the needle 252 is located within the vertical channel 162. The gasket 242 seals the tube 262 from the other portions of the extension member 134. A cleaning solution is then delivered through the needle 252 and into the vertical channel 162. The second vacuum 460 serves to facilitate the cleaning of the needle 252 by drawing a vacuum on the horizontal channel 164, which is connected to the vertical channel 162. This vacuum removes the cleaning solution from the vertical channel 162 and the needle 252.

Several sensors are used to determine the position of the cylinder assembly 190 as well as to determine the size of the container 140. A sensor 470 and a sensor 471 output data pertaining to the location of the cylinder assembly 190. The sensors 470 and 471 may be the same or additional sensors as those described above. Sensors 472, 474, and 476 are, as non-limiting examples, optical detectors that serve to determine the size of the container 140. Adjustments as to the amount of fluid delivered to the container 140 may then be made. Additionally, the amount of movement of the cylinder assembly 190 may be established so as not to damage the container 140. For example, the pressure acting on the pneumatic cylinder 124 may be limited or otherwise controlled so as to control the movement of the cylinder assembly 190.

Having described an embodiment of the filling device 100, other embodiments will now be described.

Referring to FIG. 1, the filling device 100 has been described herein as having the carriage 170 movable along the rails 120 relative to the holding mechanism 130. In another embodiment of the filling device 100, the carriage 170 is maintained in a fixed position and the holding mechanism 130 moves. For example, the holding mechanism 130 moves in the y-direction Y along the axis AA to contact the carriage 170.

The filling device 100 has been described herein as being adapted to fill containers with a fluid. It should be noted that the filling device 100 described herein may be readily adapted to remove fluids from containers.

While an illustrative and presently preferred embodiment of the invention has been described in detail herein, it is to be understood that the inventive concepts may be otherwise variously embodied and employed and that the appended claims are intended to be construed to include such variations except insofar as limited by the prior art.

I claim:

1. An apparatus for piercing a septum secured to a container, said apparatus comprising:

a holder mechanism for holding said container;

a carriage, said carriage being movable along an axis relative to said holder mechanism;

a piston attached to said carriage;

a cylinder slidably attached to said piston along said axis, with said piston residing at least partially inside said cylinder, said cylinder having a hole formed therein;

a needle attached to said piston and passing through said hole in said cylinder, said needle extending along said axis;

a chamber located within said cylinder which is formed when said cylinder is attached to said piston, said chamber being changeable in volume depending on where said piston resides within said cylinder; and said needle being in a first operative position relative to said cylinder is when said chamber has a first volume and said needle being in a second operative position relative to said cylinder when said chamber has a second volume.

2. The apparatus of claim 1 wherein said needle is retracted within said cylinder when said needle is in said first operative position and wherein said needle extends outwardly from said cylinder when said needle is in said second operative position.

3. The apparatus of claim 1 wherein said piston comprises a portion which passes through said hole in said cylinder and extends along said axis, said needle being located within said member.

4. The apparatus of claim 1 wherein said holder mechanism comprises a plurality of tiers.

5. The apparatus of claim 1 wherein said holder mechanism comprises a first hole extending along said axis, said first hole being sized and positioned to receive said needle.

6. The apparatus of claim 5 wherein said holder mechanism comprises a second hole, said second hole intersecting said first hole.

7. The apparatus of claim 6 and further comprising a fluid control device connected to said holding mechanism second hole.

8. The apparatus of claim 1 wherein said cylinder further comprises a vent hole extending between the exterior of said cylinder and said chamber.

9. The apparatus of claim 8 and further comprising a fluid control device connected to said cylinder vent hole.

10. The apparatus of claim 9, wherein said fluid control device is a pump.

11. The apparatus of claim 9, wherein said fluid control device is a valve.

12. The apparatus of claim 1 wherein said piston has a first diameter associated therewith and a piston ring extending therefrom, said piston ring having a second diameter associated therewith, said cylinder comprising an inner wall extending parallel to said axis, said inner wall having a cylinder protrusion extending therefrom, said cylinder protrusion forming an opening into said cylinder having a third diameter associated therewith, said cylinder protrusion third diameter being greater than said piston first diameter and smaller than said piston ring second diameter.

13. The apparatus of claim 1 wherein said cylinder comprises an exterior surface located opposite said piston, said exterior surface comprising a plurality of tiers formed therein, wherein at least one of said tiers is adapted to contact said container.

14. The apparatus of claim 1 wherein said cylinder comprises a groove formed therein, said groove extending parallel to said axis, said carriage comprising a protrusion extending therefrom, said protrusion being received by said groove.

15. The apparatus of claim 14 wherein said grove has a preselected length.

16. The apparatus of claim 1 wherein said cylinder is sealably and slidably attached to said piston along said axis.

17. The apparatus of claim 1 and further comprising a seal between said cylinder and said piston.

18. The apparatus of claim 1 and further comprising a seal between said needle and said piston.

19. The apparatus of claim 1 and further comprising a fluid delivery device operatively associated with said needle.

20. The apparatus of claim 1 and further comprising a fluid removal device operatively associated with said needle.

21. A method for piercing a septum sealing a container, said method comprising:

providing a holder mechanism adapted to hold said container;

providing a carriage, said carriage being movable relative to said holder mechanism along an axis;

providing a piston attached to said carriage;

providing a cylinder slidably attached to said piston along said axis, said cylinder having a cylinder hole formed therein, said attachment between said piston and said cylinder forming a chamber;

providing a needle attached to said piston and passing through said cylinder hole, said needle extending along said axis;

moving said carriage along said axis away from said holder mechanism;

filling said chamber with a fluid so that said needle retracts into said cylinder;

positioning said container within said holder mechanism;

moving said carriage along said axis to a point where said cylinder contacts said container; and moving said carriage along said axis toward said holder mechanism while venting said fluid from said chamber volume and maintaining a preselected force on said container until said needle pierces said septum.

22. The method of claim 21 and further comprising passing a fluid through said needle and into said container.

23. The method of claim 21 and further comprising evacuating said container by establishing a vacuum on said needle after said needle has pierced said septum.

24. The method of claim 21 and further comprising:

increasing the volume of said chamber to a point where said needle is removed from said container, said increasing said volume causing said carriage to move along said axis away from said holder mechanism; and moving said carriage along said axis away from said holder mechanism to a point wherein said cylinder does not contact said container.

* * * * *